(12) United States Patent
Macinga et al.

(10) Patent No.: US 10,813,357 B1
(45) Date of Patent: *Oct. 27, 2020

(54) COMPOSITIONS AND METHODS WITH EFFICACY AGAINST SPORES AND OTHER ORGANISMS

(71) Applicant: GOJO INDUSTRIES, INC., Akron, OH (US)

(72) Inventors: David R. Macinga, Stow, OH (US); James E. Bingham, Akron, OH (US)

(73) Assignee: GOJO Industries, Inc., Akron, OH (US)

( * ) Notice: Subject to any disclaimer, the term of this patent is extended or adjusted under 35 U.S.C. 154(b) by 110 days.

This patent is subject to a terminal disclaimer.

(21) Appl. No.: 15/162,886

(22) Filed: May 24, 2016

Related U.S. Application Data

(60) Provisional application No. 62/166,211, filed on May 26, 2015.

(51) Int. Cl.
*A01N 47/44* (2006.01)
*A61L 2/18* (2006.01)
*A01N 31/02* (2006.01)

(52) U.S. Cl.
CPC ............. *A01N 47/44* (2013.01); *A01N 31/02* (2013.01); *A61L 2/18* (2013.01)

(58) Field of Classification Search
CPC .................................................. A01N 47/44
See application file for complete search history.

(56) References Cited

U.S. PATENT DOCUMENTS

| | | | |
|---|---|---|---|
| 5,776,430 A | 7/1998 | Osborne et al. | |
| 5,800,827 A * | 9/1998 | Igarashi | A01N 47/44 424/405 |
| 6,653,274 B1 | 11/2003 | Godfroid et al. | |
| 6,855,678 B2 | 2/2005 | Whiteley | |
| 7,081,246 B2 | 7/2006 | Asmus et al. | |
| 7,147,873 B2 | 12/2006 | Scholz et al. | |
| 7,560,422 B2 | 7/2009 | Shapiro | |
| 7,651,990 B2 | 1/2010 | Asmus | |
| 7,655,460 B2 | 2/2010 | Rouleau et al. | |
| 7,803,390 B2 | 9/2010 | Asmus et al. | |
| 8,062,649 B2 | 11/2011 | Asmus et al. | |
| 8,198,326 B2 | 6/2012 | Scholz | |
| 8,293,802 B2 | 10/2012 | Modak et al. | |
| 8,338,491 B2 | 12/2012 | Asmus et al. | |
| 8,343,903 B2 | 1/2013 | Whiteley | |
| 8,569,384 B2 | 10/2013 | Asmus et al. | |
| 8,623,935 B2 | 1/2014 | Hobbs et al. | |
| 8,795,697 B2 | 8/2014 | Brown | |
| 8,808,722 B2 | 8/2014 | Scholz et al. | |
| 8,840,932 B2 | 9/2014 | Scholz et al. | |
| 9,028,852 B2 | 5/2015 | Scholz | |
| 2008/0260716 A1 | 10/2008 | Kritzler et al. | |

FOREIGN PATENT DOCUMENTS

WO 2001041727 A1 6/2001

OTHER PUBLICATIONS

Mulberry et al., Am. J. Infect. Control, 2001, vol. 29, pp. 377-382 (Year: 2001).*
Yamamoto et al., Am. J. Infect. Control, 2014, vol. 42, pp. 574-576 (Year: 2014).*
Gorman et al., "The sporicidal activity and inactivation of chlorhexidine gluconate in aqueous and alcoholic solution", J. Appl. Bacteriology, 1987, vol. 63, pp. 183-188 (Year: 1987).*
Russell, "Chlorhexidine: Antibacterial Action and Bacterial Resistance", Infection, 1986, vol. 14, No. 5, pp. 212-215 (Year: 1986).*
Nerandzic et al., PLoS ONE, Apr. 2015, vol. 10, No. 4, e0123809 (Year: 2015).*

* cited by examiner

*Primary Examiner* — James D. Anderson
(74) *Attorney, Agent, or Firm* — Calfee, Halter & Griswold LLP

(57) ABSTRACT

Compositions and methods for the disinfection of surfaces are provided. The compositions include a $C_{1-6}$ alcohol, and a primary enhancer selected from biguanides. The disinfectant composition is characterized by a pH of no more than about 2.5. Broad spectrum efficacy is achieved, and synergistic activity is exhibited against *C. difficile* spores.

14 Claims, 1 Drawing Sheet

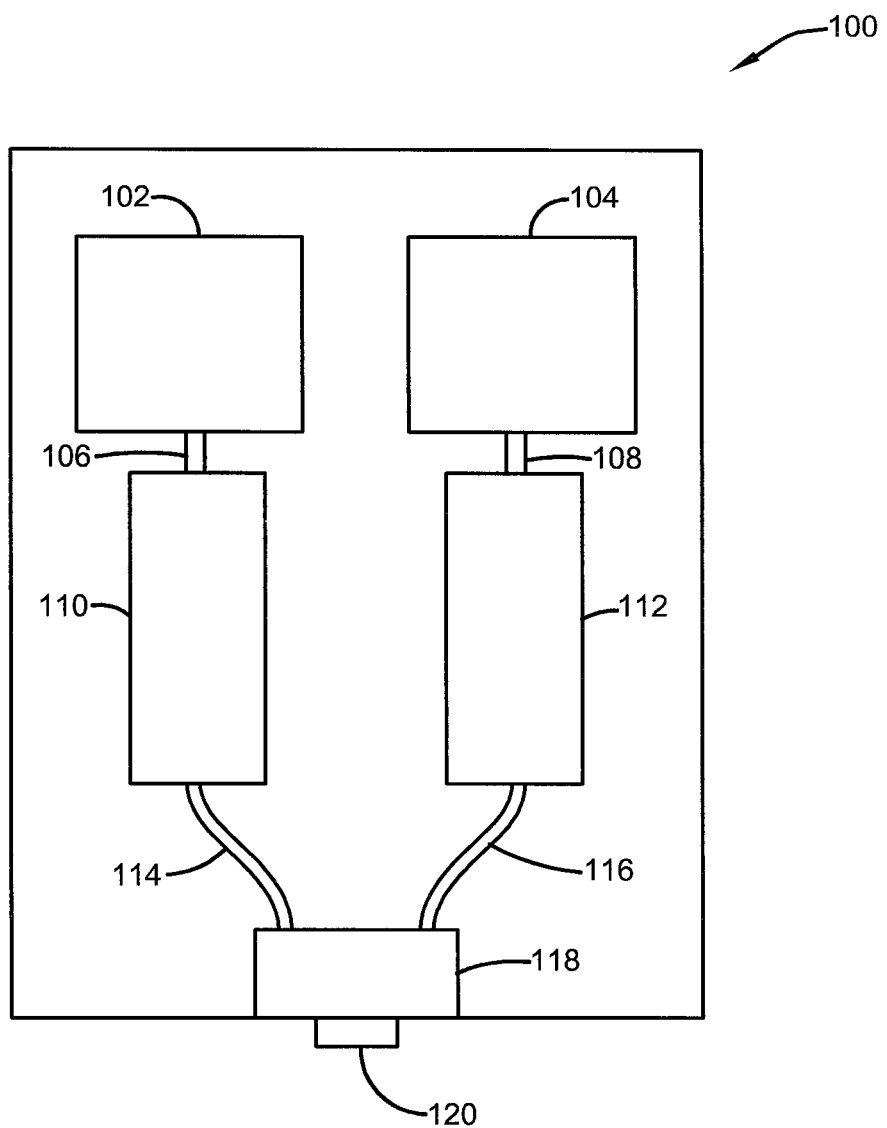

US 10,813,357 B1

COMPOSITIONS AND METHODS WITH EFFICACY AGAINST SPORES AND OTHER ORGANISMS

TECHNICAL FIELD

Embodiments of the present invention provide compositions and methods having efficacy against spores such as *Clostridium difficile* spores, and other organisms. Acidified disinfectant compositions containing a biguanide enhancer exhibit synergistic efficacy against spores such as *C. difficile* spores, and also exhibit excellent efficacy against fungi, bacteria, and viruses.

BACKGROUND OF THE INVENTION

Patients in healthcare facilities can sometimes contract serious infections. Such infections may be generally referred to as healthcare-associated infections (HAIs). While most types of HAIs are declining, one infection, caused by the bacteria *Clostridum difficile* (*C. difficile*), remains at historically high levels. *C. difficile* is a spore-forming, Gram-positive anaerobic *bacillus* of the human intestine and is thought to be present in 2-5% of the adult population. Pathogenic *C. difficile* strains produce multiple toxins, the most well-characterized of which are enterotoxin (*Clostridium difficile* toxin A) and cytotoxin (*C. difficile* toxin B), both of which can produce diarrhea and inflammation in infected patients. The emergence of a new, highly toxic strain of *C. difficile*, resistant to flouroquinolone antibiotics, such as ciprofloxacin and levofloxacin have also been reported. *C. difficile* infection causes diarrhea and other intestinal problems and is linked to 14,000 deaths in the United States each year.

Control of *C. difficile* outbreaks present significant challenges to health care facilities. *C. difficile* spores survive routine environmental cleaning with detergents and hand hygiene with alcohol-based gels. The spores can survive on surfaces for long periods of time. As a result, the bacteria can be cultured from almost any surface. Once spores are ingested, their acid-resistance allows them to pass through the stomach unscathed. They germinate and multiply into vegetative cells in the colon upon exposure to bile acids.

A variety of strategies have been proposed to kill *C. difficile* spores on various surfaces, with limited success. Bleach-based compositions have been employed for hard surfaces, and have been shown to reduce the environmental burden of *C. difficile*. but can be corrosive. Hydrogen peroxide-based compositions have also been proposed, including combinations of hydrogen peroxide and peracetic acid, a combination of hydrogen peroxide and silver cation dry-mist system, and the so-called Accelerated Hydrogen Peroxide (AHP). Peracids generally have poor stability and corrosive properties. Hydrogen peroxide is also prone to decomposition, and concentrated solutions can be highly corrosive. Alcohol-based sanitizers have not generally been effective. In fact, ethanol is sometimes used to store *C. difficile* spores.

A need remains for more stable, less corrosive compositions having good efficiency against *C. difficile* spores.

Spores and other pathogenic infectious agents such as bacteria, fungi, viruses, fungal and bacterial spores, and conformationally altered prions can be resistant to current sanitizers and cleansers. Chemical and biological warfare agents can be fast-acting and pervasive. There is a continuing need for effective, easy to use products that will be safe for humans and the environment, that can decontaminate skin, and particularly wounds, following chemical and/or biological warfare agent exposure, that can decontaminate surfaces to eliminate infectious agents such as conformationally altered prions, bacteria, fungi, viruses, and fungal and bacterial spores, and that can be used to decontaminate homes, building materials, and furniture that has been infected with black mold spores, and that can reduce the transmission of infectious pathogens.

BRIEF DESCRIPTION OF THE DRAWINGS

FIG. 1 is a schematic view of a dispenser according to the present invention.

DETAILED DESCRIPTION OF ILLUSTRATIVE EMBODIMENTS

In one or more embodiments, the present invention provides disinfectant compositions. The physical form of the disinfectant composition is not particularly limited, and in one or more embodiments, the composition may be presented as a liquid that is poured, pumped, sprayed, or otherwise dispensed, a gel, an aerosol, or a foam, including both aerosol and non-aerosol foams. The disinfectant composition of the present invention may be employed on a wide variety of surfaces or substrates, including hard surfaces, soft surfaces, non-living (inanimate) surfaces, living tissue, skin, soil, porous, and non-porous surfaces. For purposes of this specification, the term "surface" should be understood to include skin. The compositions of the invention may be employed to disinfect or otherwise sanitize inanimate objects such as instruments, medical equipment, furniture, handrails, textiles, etc. In one or more embodiments, the disinfectant composition may be presented as a wipe, i.e. a tissue or cloth that is wiped over a surface.

The disinfectant compositions comprise at least one $C_{1-6}$ alcohol, i.e. an alcohol containing 1 to 6 carbon atoms. Such alcohols may be referred to as lower alkanols. Typically, these alcohols have antimicrobial properties. Examples of lower alkanols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the disinfectant compositions comprise a mixture of alcohols. In one or more embodiments, the disinfectant compositions comprise a mixture of ethanol and isopropanol. In one or more embodiments, the disinfectant compositions comprise butanol. In one or more embodiments, the disinfectant compositions comprise a mixture of ethanol and butanol. In one or more embodiments, the disinfectant compositions comprise a mixture of n-butanol and isopropanol.

In one or more embodiments, the disinfectant composition comprises at least about 10 percent by weight (wt. %) alcohol, based upon the total weight of the disinfectant composition. In one or more embodiments, the disinfectant composition comprises at least about 15 wt. % alcohol, In one or more embodiments, the disinfectant composition comprises at least about 20 wt. % alcohol, in another embodiment, the disinfectant composition comprises at least about 25 wt. % alcohol, in yet another embodiment, the disinfectant composition comprises at least about 30 wt. % alcohol, and in still yet another embodiment, the disinfectant composition comprises at least about 35 wt. % alcohol, based upon the total weight of disinfectant composition. In one or more embodiments, the disinfectant composition comprises at least about 50 wt. % alcohol, in another embodiment, at least about 55 wt. %, in another embodiment, the disinfectant composition comprises at least about 60 wt. % alcohol, in another embodiment, the disinfectant composition comprises at least about 65 wt. % alcohol, in yet another embodiment, the disinfectant composition comprises at least about 70 wt. % alcohol, and in still yet another embodiment, the disinfectant composition comprises at least about 75 wt. % alcohol, based upon the total weight of disinfectant composition.

In one embodiment, the disinfectant composition comprises less than about 90 wt. % alcohol, in another embodiment, the disinfectant composition comprises less than about 85 wt. % alcohol, in another embodiment, the disinfectant composition comprises less than about 80 wt. % alcohol. More or less alcohol may be required in certain instances, depending particularly on other ingredients and/or the amounts thereof employed in the composition.

In certain embodiments, the disinfectant composition comprises from about 10 wt. % to about 90 wt. % alcohol, in other embodiments, from about 15 wt. % to about 85 wt. % alcohol, in other embodiments, the disinfectant composition comprises from about 20 wt. % to about 85 wt. % of alcohol, in other embodiments, from about 30 wt. % to about 85 wt. %, in yet other embodiments, the disinfectant composition comprises from about 60 wt. % to about 78 wt. % of alcohol, and in still other embodiments, the disinfectant composition comprises from about 65 wt. % to about 75 wt. % of alcohol, based upon the total weight of the disinfectant composition.

In any of the above embodiments, the disinfectant composition may include a biguanide. Examples of biguanide enhancers include chlorhexidine salts, such as chlorhexidine gluconate, as well as the digluconate, diacetate, dimethosulfate, and dilactate salts, and combinations thereof. Cationic antimicrobial agents such as chlorhexidine gluconate are further described in International Pat. Appl. Pub. No. WO 2009/088894 A2, which is hereby incorporated by reference. Polymeric biguanides are also known, such as those described in U.S. Pat. No. 6,303,557, which is hereby incorporated by reference.

In one or more embodiments, the amount of biguanide is at least 0.05 percent by weight (wt. %), in other embodiments, at least 0.1 wt. %, in other embodiments, at least 0.25 wt. %, and in other embodiments, at least 0.5 wt. %, based upon the total weight of the composition. In one or more embodiments, the amount of biguanide is less than about 8 wt. %, in other embodiments, less than about 6 wt. %, and in other embodiments, less than about 4 wt. %, based upon the total weight of the composition.

In any of the above embodiments, the disinfectant composition may include one or more secondary enhancers. Compounds that enhance the efficacy of acidified alcoholic compositions are further described in co-pending patent application Ser. No. 14/615,552, filed on Feb. 6, 2015, which is hereby incorporated by reference. Examples of secondary enhancers include protein denaturants. Examples of secondary enhancers include chaotropic agents. Examples of secondary enhancers include amine-containing enhancers, α-aminoacids, salts of alkali metals, salts of alkaline earth metals, anionic surfactants, and quaternary biocides.

In any of the above embodiments, the disinfectant composition may include an amine-containing enhancer. Examples of amine-containing enhancers include urea, thiourea, dimethyl urea, guanidine-HCl, guanidine thiocyanate, aminoguanidine bicarbonate, guanidine carbonate, guanidine phosphate, L-NG-nitroarginine, and aminoguanidine-HCL.

In any of the above embodiments, the disinfectant composition may include an α-aminoacid. Examples of α-aminoacids include sulfur-containing aminoacids and nitro-containing aminoacids. Examples of sulfur-containing aminoacids include L-cysteine and methionine. Examples of nitro-containing aminoacids include L-NG-nitroarginine.

In any of the above embodiments, the disinfectant composition may include one or more salts of alkali metals or alkaline earth metals. Examples of salts include ammonium chloride, ammonium iron citrate, calcium chloride, iron perchlorate, lithium perchlorate, lithium acetate, magnesium chloride, sodium chlorate, sodium chloride, sodium chlorite, and tris-HCl (tris is 2-Amino-2-hydroxymethyl-propane-1, 3-diol).

In any of the above embodiments, the disinfectant composition may include one or more anionic surfactants. Anionic surfactants include sodium lauryl sulfate (SLS) (also known as sodium dodecyl sulfate (SDS)) and sodium laureth sulfate (SLES).

Advantageously, a synergistic sporicidal effect is observed when the enhancer is combined with alcohol at an acidic pH. In certain embodiments, enhancers that exhibit little or no efficacy on their own against *C. difficile* spores provide an enhanced efficacy when combined with alcohol according to the present invention, and a further enhanced efficacy when the pH of the disinfectant composition is less than 7. It has surprisingly been found that, while disinfectant compositions show little or no efficacy against the spores, the combination of an enhancer and alcohol at a low pH exhibits synergistically enhanced efficacy against *C. difficile* spores.

The amount of enhancer is not particularly limited, so long as it is at least an efficacy-enhancing amount. The minimum amount of enhancer that corresponds to an efficacy-enhancing amount can be determined by comparing the log kill of spores achieved by a composition comprising an alcohol to a composition comprising an alcohol and a given amount of enhancer. The amount of enhancer below which no difference in log kill is seen is an efficacy-enhancing amount. In other words, rapid sporicidal efficacy is observed at lower concentrations of alcohol when an enhancer is present compared to when the enhancer is not present.

In one embodiment, the enhancer is added in an amount of from about 0.1 to about 20 wt. %, based upon the total weight of the disinfectant composition. In another embodiment, the amount of enhancer is from about 0.25 to about 15 wt. %, and in yet another embodiment, from about 0.5 to about 12 wt. %, based upon the total weight of the disinfectant composition. It will be understood that greater levels of enhancer can be used, if desired, and are expected to perform equally as well.

In one or more of the above embodiments, the enhancer comprises urea. In one or more of the above embodiments, the enhancer comprises guanidine-HCl. In one or more of the above embodiments, the enhancer comprises aminoguanidine-HCl. Combinations of secondary enhancers may also be employed.

Additional examples of secondary enhancers include nonionic surfactants, such as decyl glucoside and polyalkoxylated dimethicones including PEG-12 dimethicone. Examples of secondary enhancers also include organic acids, such as citric acid, lauric acid, tannic acid, and iodoacetic acid. Examples of secondary enhancers include also include auxiliary antimicrobial agents. Examples of secondary enhancers include also include oxidizing agents such as sodium nitrite. In one or more embodiments, the secondary enhancer includes glycerol.

Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis (2-ethylhexyl)-5-methyl-hexahydropyrimidine; chlorhexidine salts including chlorhexidine gluconate and the salts of N,N"-Bis(4-chlorophenyl)-3,12-diimino-2,4,11, 14-tetraazatetradecanediimidiamide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, $C_{6-10}$-alkane diols such as hexanediol, octanediol, and decanediol, and mixtures thereof. In any of the above embodiments, the disinfectant composition may include a quaternary biocides. Examples of quaternary biocide enhancers include benzalkonium chloride.

In one or more embodiments, the about of auxiliary antimicrobial agent is from about 0.1 to about 1 wt. %, based upon the total weight of the disinfectant composition.

In one or more of the above embodiments, the pH of the disinfectant composition is less than about 2.5; in one or more embodiments, the pH of the disinfectant composition is less than about 2; in one or more embodiments, the pH of the disinfectant composition is less than about 1.8. In one or more of the above embodiments, the pH of the disinfectant composition is from about 0 to about 2.5. In one or more of the above embodiments, the pH of the disinfectant composition from about 0.5 to about 2. In one or more of the above embodiments, the pH of the disinfectant composition from about 1 to about 1.8. The disinfectant composition may therefore be referred to as acidified, since the disinfectant composition has an acidic pH.

The disinfectant composition may be acidified by the addition of one or more acids. The type of acid is not limited, however, weak acids are not preferred. The acid should have a pKa of 5.4 (the pKa of citric acid) or less.

Examples of useful acidifying agents include mineral acids and organic acids. Mineral acids include, without limitation, hydrochloric acid, nitric acid, phosphoric acid, phosphonic acid, boric acid, and sulfuric acid. Organic acids include sulfonic acids, organophosphorus acids, carboxylic acids such as benzoic acids, propionic acids, phthalic acids, butyric acids, acetic acids, amino acids, and other substituted and unsubstituted organic acids.

Examples of organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxoglutaric acid, dl-glyceric acid, and 2,5 furandicarboxylic acid.

It has been found that, in certain embodiments, acidifying the disinfectant composition enhances the efficacy of the alcoholic solutions against *C. difficile*.

The composition can further comprise a wide range of optional ingredients, with the proviso that they do not deleteriously affect the sanitizing efficacy of the composition. By deleterious is meant that the decrease in the log reduction is not de minimus, or in other words, the log reduction of *C. difficile* spores does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, foam surfactants, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

It has been discovered that the combination of alcohol and enhancer at low pH exhibits enhanced antimicrobial efficacy. Advantageously, auxiliary antimicrobials, some of which can be harsh on skin, are not required. In certain embodiments, the disinfectant composition does not contain any auxiliary antimicrobial ingredients. Any antimicrobial ingredient other than the combination of alcohol, enhancer and acid may be referred to as an auxiliary antimicrobial agent. In one embodiment, the amount of auxiliary antimicrobial agent (including preservatives) is less than about 0.1 wt. %, in other embodiments, less than about 0.05 wt. %, in other embodiments, less than about 0.01 wt. %, based upon the total weight of the disinfectant composition. In another embodiment, the disinfectant composition is devoid of auxiliary antimicrobial agents.

Advantageously, certain ingredients that have been designated as critical to current sporicidal compositions can be limited in the disinfectant composition of the present invention. For example, hypochlorous acid and precursors thereof are not necessary, and can be limited, if desired, to less than about 0.5 wt. %, or in another embodiment to less than about 0.1 wt. %, based upon the total weight of the disinfectant composition. In another embodiment, the disinfectant composition is devoid of hypochlorous acid.

In one or more embodiments, the amount of peroxyacids such as peracetic acid may be limited. When limited, in one or more embodiments, the amount of peroxyacid may be less than 0.125 wt. %, in other embodiments less than about 0.08 wt. %, based upon the total weight of the disinfectant composition. In another embodiment, the disinfectant composition is devoid of peroxyacid.

In one or more embodiments, the amount of peroxide may be limited, if desired, to less than about 0.5 wt. %, or other embodiments to less than about 0.1 wt. %, based upon the total weight of the disinfectant composition. In another embodiment, the disinfectant composition is devoid of peroxide.

Indeed, any component other than the alcohol, enhancer, acidifier, and optionally a secondary enhancer, is not necessary to achieve antimicrobial efficacy and can optionally be limited to less than about 0.5 wt. %, if desired to less than about 0.1 wt. %, if desired to less than about 0.01 wt. %, or if desired to less than about 0.001 wt. %. It will be understood that the balance of the disinfectant composition may, in certain embodiments, include water or other suitable solvent. In one embodiment, the disinfectant composition is devoid of any component other than alcohol, enhancer, acidifier, and optionally water or other suitable solvent.

The disinfectant composition may be prepared by simply mixing the components together. In one embodiment, where one or more components is obtained as a solid powder, the disinfectant composition may be prepared by a method comprising dispersing the solid powder in water or alcohol with slow to moderate agitation, and then adding other ingredients as desired, and mixing until the mixture is homogeneous.

In one embodiment, where the disinfectant composition is in liquid form, the percent solids of the disinfectant composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

Advantageously, it has been found that compositions according to the present invention have efficacy against a broad spectrum of gram positive and gram negative bacteria, fungi, parasites, fungal and bacterial spores, enveloped and non-enveloped viruses, and prions (CJD, CWD, BSE, Scrapie). One or more embodiments of the present invention exhibit efficacy against one or more of spores of *Bacillus anthracis, Bacillus cereus, Clostridium difficile, Clostridium botulinum*, and *Clostridium tetani*.

Unexpectedly, when an enhancer is combined with alcohol at a low pH, according to the present invention, sporicidal activity is enhanced, i.e. potentiated. In one or more embodiments, the disinfectant composition is effective at killing *C. difficile* spores. In one or more embodiments, the disinfectant composition is also effective in killing gram negative and gram positive bacteria, fungi, parasites, non-enveloped and enveloped viruses. In one or more embodiments, the disinfectant composition has rapid antimicrobial efficacy against bacteria such as *Staphylococcus aureus*, methicillin-resistant *S. aureus, Escherichia coli, Pseudomonas aeruginosa, Serratia marcescens*, fungi such as *Candida albicans* and *Aspergillus niger*, and black mold spores *Stachybotrys chartanim*. In one or more embodiments, the disinfectant composition has rapid efficacy against skin microflora, including resident and transient skin microflora.

Thus, the present invention further provides a method for killing or inactivating microbes such as *C. difficile* spores on a surface comprising applying, to the surface, an effective amount of a disinfectant composition as described herein. The disinfectant composition may be employed on a wide variety of surfaces or substrates, including hard surfaces, soft surfaces, skin, porous, and non-porous surfaces.

In one or more embodiments, the method provides a log reduction against spores of at least about 1 in less than about 1 minute. In other embodiments, the method provides a log reduction against spores of at least about 1.5 in less than about 1 minute. In yet other embodiments, the method provides a log reduction against the mixture of at least about 2 in less than about 1 minute. In other embodiments, the method provides a log reduction against spores of at least about 2.5 in less than about 1 minute. In yet other embodiments, the method provides a log reduction against spores of at least about 3 in less than about 1 minute.

In one or more embodiments, the method provides a log reduction against spores of at least about 1 in less than about 30 seconds. In other embodiments, the method provides a log reduction against spores of at least about 1.5 in less than about 30 seconds. In yet other embodiments, the method provides a log reduction against the mixture of at least about 2 in less than about 30 seconds. In other embodiments, the method provides a log reduction against spores of at least about 2.5 in less than about 30 seconds. In yet other embodiments, the method provides a log reduction against spores of at least about 3 in less than about 30 seconds.

In one or more embodiments, the method provides a log reduction against *C. difficile* spores of at least about 1 in less than about 1 minute. In other embodiments, the method provides a log reduction against *C. difficile* spores of at least about 1.5 in less than about 1 minute. In yet other embodiments, the method provides a log reduction against the mixture of at least about 2 in less than about 1 minute. In other embodiments, the method provides a log reduction against *C. difficile* spores of at least about 2.5 in less than about 1 minute. In yet other embodiments, the method provides a log reduction against *C. difficile* spores of at least about 3 in less than about 1 minute.

In one or more embodiments, the method provides a log reduction against *C. difficile* spores of at least about 1 in less than about 30 seconds. In other embodiments, the method provides a log reduction against *C. difficile* spores of at least about 1.5 in less than about 30 seconds. In yet other embodiments, the method provides a log reduction against the mixture of at least about 2 in less than about 30 seconds. In other embodiments, the method provides a log reduction against *C. difficile* spores of at least about 2.5 in less than about 30 seconds. In yet other embodiments, the method provides a log reduction against *C. difficile* spores of at least about 3 in less than about 30 seconds.

The methods of the present invention include the step of applying an disinfectant composition to a surface.

Advantageously, good efficacy is achieved by the methods of the present invention when the disinfectant composition is applied to the surface at standard temperature and at close to standard pressure. In one or more embodiments, the temperature of the disinfectant composition when applied to the surface may be less than about 150° F., in other embodiments, less than about 120° F., and in other embodiments, less than about 105° F. In one or more embodiments, the temperature of the disinfectant composition may be in the range of from about 40° F. to about 150° F., in other embodiments in the range of from about 40° F. to about 105° F., and in other embodiments, in the range of about 70° F. to 105° F.

Although the liquid disinfectant compositions of the present invention may be applied to the surface to be cleaned by spraying, no high pressure application is required. During this step, the disinfectant composition may be brought into contact with the target surface in bursts or in a continuous manner by circulating, flooding, spraying, foaming or fogging. The step may also be carried out by forming a two phase annular mist of antimicrobial treatment solution and air.

Advantageously, the methods of the present invention provide good efficacy against spores within 5 minutes or less. Embodiments of the invention provide good efficacy against spores within 2 minutes or less. Embodiments of the invention provide good efficacy against spores within 1 minute or less. Embodiments of the invention provide good efficacy against spores within 30 seconds or less. Advantageously, the methods of the present invention provide good efficacy against *C. difficile* spores within 5 minutes or less. Embodiments of the invention provide good efficacy against *C. difficile* spores within 2 minutes or less. Embodiments of the invention provide good efficacy against *C. difficile* spores within 1 minute or less. Embodiments of the invention provide good efficacy against *C. difficile* spores within 30 seconds or less. Thus, in one or more embodiments, the duration of contact of the disinfectant composition with the target surface is from about 20 seconds to 5 minutes, in other embodiments, from about 25 seconds to about 2 minutes, and in other embodiments, from about 30 seconds to about 1 minute. It will be understood that, in some embodiments, a longer contact time is advantageous, and in one or more embodiments, the contact time may be up to 30 minutes, and in other embodiments, up to about 60 minutes.

The amount of disinfectant composition to be applied to the target surface is not particularly limited. At a minimum, a sufficient amount of disinfectant composition should be applied to substantially wet the surface such that the surface will remain wet for the desired contact time, noting that there will be some evaporation of the disinfectant composition.

Any amount of the disinfectant composition may be used for each application, so long as it is at least an effective amount to contact substantially the entire target surface and keep it wet for a contact time of at least 30 to 60 seconds. In one or more embodiments, the amount of the disinfectant composition is sufficient to contact substantially the entire target surface and keep it wet for a contact time of at least 5 minutes. In one or more embodiments, the amount of the disinfectant composition is sufficient to contact substantially the entire target surface and keep it wet for a contact time of at least 30 minutes. In one or more embodiments, the amount of the disinfectant composition is sufficient to contact substantially the entire target surface and keep it wet for at least 60 minutes.

In one or more embodiments, the sporicidal disinfectant composition may be prepared by combining two or more liquid pre-mix compositions. A first pre-mix composition may comprise a concentrate of the primary enhancer, and a second pre-mix composition may comprise a concentrate of the alcohol, such that combination of the pre-mix compositions results in an disinfectant composition comprising alcohol and a primary enhancer as described hereinabove.

In other embodiments, a first pre-mix composition may comprise a concentrate of the alcohol and primary enhancer, and the second pre-mix composition may comprise a diluent, such that combination of the pre-mix compositions results in an disinfectant composition comprising alcohol and a primary enhancer at the concentrations as described hereinabove.

The pre-mix components may be dispensed from physically separate packages or from a unitary package having non-communicating chambers. For purposes of this specification, the term dual dispenser apparatus refers to a configuration where multiple liquid components are dispensed from a plurality of physically separate packages, and also refers to a configuration where multiple liquid components are dispensed from a unitary package having a plurality of non-communicating chambers, each chamber having an orifice through which an aliquot of a component is dispensed.

In one or more embodiments, aliquots of the pre-mix components are dispensed substantially simultaneously, such that the liquid aliquots are commingled. In particular embodiments, the aliquots are dispensed through orifices that are configured to enable the commingling of the aliquots. It will be understood that the dispenser may take a variety of forms, and may include a variety of components and configurations in order to cause the desired comingling of aliquots of the pre-mix components and dispensing of a product.

One embodiment of an exemplary dispenser is shown in FIG. 1 and is generally indicated by the numeral 100. Dispenser 100 may include a first reservoir 102 containing a first liquid pre-mix component (e.g. concentrated primary enhancer pre-mix component), and a second reservoir 104 containing a second liquid pre-mix component (e.g. alcoholic diluent pre-mix component). The pH-adjusting agent may be present in either or both of the pre-mix components. As will be apparent to those skilled in the art, and as indicated above, the first and second reservoirs 102 and 104 are not in direct communication with one another, and the first and second pre-mix components are therefore stored separately within the dispenser. Although separate reservoirs are shown in FIG. 1, it is contemplated that the first and second reservoirs 102 and 104 may be provided as physically separate chambers in a single package. Each of the first and second reservoirs 102 and 104 is impervious to fluid transfer therethrough, except through inlet passages 106 and 108, respectively.

In one or more embodiments, the present invention provides a method of preparing an disinfectant composition, the method comprising the steps of providing a dispenser having a first reservoir containing a first liquid pre-mix, and a second reservoir containing a second liquid pre-mix, wherein the dispenser is adapted to dispense an aliquot of the first pre-mix and an aliquot of the second pre-mix, such that the aliquots commingle. Upon commingling, the aliquots of the first pre-mix and second pre-mix form an disinfectant composition comprising an alcohol and a primary enhancer at a pH of less than about 5.

In certain embodiments, a first pump 110 may be in fluid communication with the first reservoir 102 through the inlet passage 106, and a second pump 112 may be in fluid communication with the second reservoir 104 through the inlet passage 108. First and second pumps 110 and 112 may be any type of pump known to those skilled in the art and suitable for conveying the first and second liquid pre-mix components from the first and second reservoirs 102 and 104. In one or more embodiments, the pumps 110 and 112 may both be positive displacement pumps. The first and second pumps 110 and 112 discharge the first and second pre-mix components through outlet passages 114 and 116, respectively. In certain embodiments, the output or displacement of the first and second pumps 110 and 112 may be adjustable to vary the rate of fluid flow therethrough. While the exemplary dispenser 100 shown and described includes first and second pumps 110 and 112, it is also contemplated that a single pump may be used, and may be in fluid communication with both the first and second reservoirs 102 and 104.

The outlet passages 114 and 116 may each extend to a mixing nozzle 118 where the first and second pre-mix components are comingled to form an disinfectant composition. The features and dimensions of the mixing nozzle 118 may be adjusted to vary the volume of each pre-mix aliquot, as well as the rate of mixing and comingling of the first and second pre-mix components. The mixing nozzle 118 includes a dispensing passage 120 through which the disinfectant composition is dispensed.

In certain embodiments, the first and second pumps 110 and 112 may be adjusted to produce substantially the same flow rate of the first and second pre-mix components therethrough. In other embodiments, the pumps 110 and 112 may be adjusted to provide different flow rates, and in certain embodiments, the pre-mix components may be dispensed sequentially.

In certain embodiments, the first and second pumps 110 and 112 may be adjusted to select substantially the same aliquot volume for the first and second pre-mix components. In other embodiments, the pumps 110 and 112 may be adjusted to provide different aliquot volumes.

In one or more embodiments, the first and second pumps 110 and 112 may be adapted to dispense a single dose of composition upon actuation. In the same or other embodiments, the first and second pumps 110 and 112 may be adapted to produce a continuous flow of the disinfectant composition upon actuation.

In one or more embodiments, the first pre-mix may include a concentrated form of the compositions of the present invention, and the second pre-mix may include a diluent, such that upon being dispensed, the combination forms a composition that includes the amounts of components taught herein.

Advantageously, embodiments of the present invention provide easy to use products that are safe for humans and the environment, and that can decontaminate skin, and particularly wounds. Following chemical and/or biological warfare agent exposure, embodiments of the present invention can contain and/or destroy the agent, preventing cutaneous penetration and further contamination. Embodiments of the present invention can decontaminate surfaces to eliminate infectious agents such as conformationally altered prions, bacteria, fungi, viruses, and fungal and bacterial spores, and that can be used to decontaminate homes, building materials, and furniture that has been infected with black mold spores. Embodiments of the present invention can reduce the transmission of infectious pathogens.

In order to demonstrate the practice of the present invention, the following examples have been prepared and tested. The examples should not, however, be viewed as limiting the scope of the invention. The claims will serve to define the invention.

Examples

Samples were prepared according to the compositions shown in Table 1 below (pH adjusted with 12 N hydrochloric acid, and q.s. water), and tested for efficacy against *C. difficile* spores, according to the ASTM E2783-11: "Standard Test Method for Assessment of Antimicrobial Activity for Water Miscible Compounds Using a Time-Kill Procedure." Temperature was room temperature. Results are shown in Table 1.

TABLE 1

| Example No. | Ethanol (wt. %) | CHG (wt. %) | Total Sample Weight | Target pH | Exposure Time (s) | $Log_{10}$ Reductions (CFU/ml) |
|---|---|---|---|---|---|---|
| Comp. A | 70% Ethanol (39.65 g) | — | 50 g | 1.5 | 60 | 0.34 |
| Comp. B | — | 1.0% CHG (2.5 g) | 50 g | 1.5 | 60 | 0.35 |
| Comp. C | 70% Ethanol (39.65 g) | — | 50 g | 3.0 | 60 | −0.21 |
| Comp. D | 70% Ethanol (39.65 g) | 1.0% CHG (2.5 g) | 50 g | 3.0 | 60 | 0.04 |
| 1 | 70% Ethanol (39.65 g) | 0.1% CHG (0.25 g) | 50 g | 1.5 | 30 | 1.69 |
| 2 | 70% Ethanol (39.65 g) | 0.25% CHG (0.625 g) | 50 g | 1.5 | 30 | 1.76 |
| 3 | 70% Ethanol (39.65 g) | 0.5% CHG (1.25 g) | 50 g | 1.5 | 30 | 2.04 |
| 4 | 70% Ethanol (39.65 g) | 1.0% CHG (2.5 g) | 50 g | 1.5 | 30 | 1.80 |
| 5 | 70% Ethanol (39.65 g) | 2.0% CHG (5.0 g) | 50 g | 1.5 | 30 | 1.51 |
| 6 | 70% Ethanol (39.65 g) | — | 50 g | 1.5 | 30 | 0.71 |
| 1 | 70% Ethanol (39.65 g) | 0.1% CHG (0.25 g) | 50 g | 1.5 | 60 | 3.24 |
| 2 | 70% Ethanol (39.65 g) | 0.25% CHG (0.625 g) | 50 g | 1.5 | 60 | >3.54 |
| 3 | 70% Ethanol (39.65 g) | 0.5% CHG (1.25 g) | 50 g | 1.5 | 60 | >3.54 |
| 4 | 70% Ethanol (39.65 g) | 1.0% CHG (2.5 g) | 50 g | 1.5 | 60 | >3.54 |
| 5 | 70% Ethanol (39.65 g) | 2.0% CHG (5.0 g) | 50 g | 1.5 | 60 | >3.54 |
| 6 | 70% Ethanol (39.65 g) | — | 50 g | 1.5 | 60 | 1.29 |

Various modifications and alterations that do not depart from the scope and spirit of this invention will become apparent to those skilled in the art. This invention is not to be duly limited to the illustrative embodiments set forth herein.

What is claimed is:

1. A acidified composition for inactivation of *C. difficile* spores, the acidified composition comprising:
   at least 10 wt. % of a $C_{1-6}$ alcohol,
   from 0.1 to 20 wt. % of a primary enhancer consisting of one or more chlorhexidine salts, and
   one or more acids,
   wherein the acidified composition has a pH of no more than 2.5.

2. The acidified composition of claim 1, wherein the $C_{1-6}$ alcohol is selected from the group consisting of ethanol, isopropanol, and combinations thereof.

3. The acidified composition of claim 1, wherein the acidified composition comprises at least 30 wt. % of the $C_{1-6}$ alcohol, based upon the total weight of the acidified composition.

4. The acidified composition of claim 1, wherein the acidified composition comprises at least 50 wt. % of the $C_{1-6}$ alcohol, based upon the total weight of the acidified composition.

5. The acidified composition of claim 1, wherein the acidified composition further comprises a secondary enhancer that is selected from the group consisting of amine-containing enhancers, α-aminoacids, salts of alkali metals, salts of alkaline earth metals, anionic surfactants, and combinations thereof.

6. The acidified composition of claim 1, wherein the pH of the acidified composition is from 0.5 to 2.

7. The acidified composition of claim 1, wherein the $C_{1-6}$ alcohol is selected from the group consisting of ethanol, isopropanol, and combinations thereof, and wherein the one or more chlorhexidine salts consists of chlorhexidine gluconate.

8. The acidified composition of claim 1, wherein the acidified composition comprises from 60 to 78 wt. % of the $C_{1-6}$ alcohol, based upon the total weight of the acidified composition.

9. A method for inactivation of *C. difficile* spores comprising:
 contacting the spores with an acidified disinfectant composition comprising:
 at least 10 wt. % of a $C_{1-6}$ alcohol,
 from 0.1 to 20 wt. % of a primary enhancer consisting of one or more chlorhexidine salts, and
 one or more acids,
 wherein the acidified disinfectant composition has a pH of less than 2.5.

10. The method of claim 9, wherein the $C_{1-6}$ alcohol is selected from the group consisting of ethanol, isopropanol, and combinations thereof.

11. The method of claim 9, wherein the acidified disinfectant composition comprises at least 50 wt. % of the $C_{1-6}$ alcohol, based upon the total weight of the acidified disinfectant composition.

12. The method of claim 9, wherein the acidified disinfectant composition further comprises a secondary enhancer that is selected from the group consisting of amine-containing enhancers, α-aminoacids, salts of alkali metals, salts of alkaline earth metals, anionic surfactants, and combinations thereof.

13. The method of claim 9, wherein the one or more chlorhexidine salts consists of chlorhexidine gluconate.

14. The method of claim 9, wherein the acidified disinfectant composition further comprises a secondary enhancer selected from the group consisting of non-ionic surfactants, auxiliary antimicrobial agents, organic acids, oxidizing agents, and combinations thereof.

* * * * *